(12) United States Patent
Ziegler et al.

(10) Patent No.: US 9,170,192 B2
(45) Date of Patent: Oct. 27, 2015

(54) SYSTEMS AND METHODS FOR IDENTIFYING MATERIALS UTILIZING MULTIVARIATE ANALYSIS TECHNIQUES

(76) Inventors: Lawrence D. Ziegler, Wellesley, MA (US); Ishan S. Patel, Westborough, MA (US)

(\*) Notice: Subject to any disclaimer, the term of this patent is extended or adjusted under 35 U.S.C. 154(b) by 1361 days.

(21) Appl. No.: 12/902,196

(22) Filed: Oct. 12, 2010

(65) Prior Publication Data

US 2011/0087439 A1   Apr. 14, 2011

Related U.S. Application Data

(60) Provisional application No. 61/250,130, filed on Oct. 9, 2009.

(51) Int. Cl.
| | | |
|---|---|---|
| *G01N 33/48* | (2006.01) | |
| *G01N 21/35* | (2014.01) | |
| *G06F 19/16* | (2011.01) | |
| *G01N 21/65* | (2006.01) | |
| *G01N 21/3563* | (2014.01) | |

(52) U.S. Cl.
CPC ............... *G01N 21/35* (2013.01); *G01N 21/65* (2013.01); *G06F 19/16* (2013.01); *G01N 21/3563* (2013.01); *G01N 2021/3595* (2013.01)

(58) Field of Classification Search
CPC ....................................................... G06F 19/16
USPC ............................................................ 702/19
See application file for complete search history.

(56) References Cited

U.S. PATENT DOCUMENTS

2006/0240572 A1   10/2006   Carron et al.
2006/0275541 A1   12/2006   Weimer

OTHER PUBLICATIONS

I.S. Patel, et al., Barcoding Bacterial Cells: A SERS-Based Methodology for Pathogen Identifiction, Published online Oct. 17, 2008, pp. 1660-1672, Journal of Raman Spectroscopy.

*Primary Examiner* — Jerry Lin
(74) *Attorney, Agent, or Firm* — Schmeiser, Olsen & Watts LLP

(57) ABSTRACT

Described are a system and method for identifying a material. A spectrum is received. A barcode is generated from a sign of a second derivative of the spectrum. Multivariate data analysis tools and techniques are applied based on the barcode. The material is identified from results of the multivariate data analysis based on the barcode.

19 Claims, 11 Drawing Sheets

SYSTEMS AND METHODS FOR IDENTIFYING MATERIALS UTILIZING MULTIVARIATE ANALYSIS TECHNIQUES

RELATED APPLICATIONS

This application claims priority to and the benefit of U.S. provisional patent application No. 61/250,130, filed Oct. 9, 2009, the contents of which are incorporated herein by reference in their entirety.

FIELD OF THE INVENTION

The present invention relates generally to the identification of chemical and biological materials, and more specifically to systems and methods that detect and identify such materials in a sample by applying spectral barcode inputs to multivariate analysis tools and techniques.

BACKGROUND

Vibrational spectroscopic techniques such as Raman Spectroscopy in its various forms, including resonance Raman and surface enhanced Raman spectroscopy (SERS), are well-known for identifying samples, which contain unknown materials or substances, ranging from simple molecular compounds to more complex structures. Since different samples exhibit unique vibrational spectra, harmful materials, for example, can be identified by detection devices, such as Raman or IR devices, without the need to physically contact the material or add labeling chemical agents. This feature permits law enforcement personnel, public health agencies, medical personnel, and the military to identify contraband narcotics, explosives, poisons, pathogens, and toxic chemicals with minimal risk. In SERS, as a molecule approaches a roughened metal surface, the intensity of its Raman spectra is enhanced. Thus, SERS offers the advantage of sensitivity in addition to the specificity of normal Raman or IR.

However, conventional spectral signal analysis techniques often cannot distinguish spectra between closely-related samples. Thus, identification errors can occur when spectroscopic signatures are produced for closely-related spectra. For example, two different spectra may incorrectly appear to be identical on a principle component analysis (PCA) plot.

BRIEF SUMMARY

An embodiment of the invention features a computer-implemented method of identifying a material. A spectrum is received. A barcode is generated from a sign of a second derivative of the spectrum. Multivariate data analysis based on the barcode is performed. The material is identified from results of the multivariate data analysis based on the barcode.

Another embodiment of the invention features a system for identifying a material. The system comprises a barcode converter and a spectra analyzer. The barcode converter receives a spectrum and generates a barcode based on a sign of a second derivative of the spectrum. The spectra analyzer performs multivariate analysis on the barcode.

Another embodiment of the invention features a computer program product for testing software under development. The computer program product comprises a computer readable storage medium having computer readable program code embodied therewith. The computer readable program code comprises computer readable program code configured to receive a spectrum. The computer readable program code comprises computer readable program code configured to generate a barcode based on thr sign of the second derivative of the spectrum. The computer readable program code comprises computer readable program code configured to perform a multivariate analysis in response to the barcode.

BRIEF DESCRIPTION OF THE SEVERAL VIEWS OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIG. 3 is a plot of SERS spectra of four members of a group of closely related bacteria.

FIG. 6 is a graph illustrating averaged barcodes derived from the SERS spectra of FIG. 3 for each bacteria sample.

FIG. 8A is a DFA plot of the *cereus* group SERS barcode training set illustrating positive identification of a *B. anthracis* Sterne SERS spectral signature.

FIG. 8B is an dendrogram corresponding to the DFA scatter plot shown in FIG. 8A.

DETAILED DESCRIPTION

Figure 1:
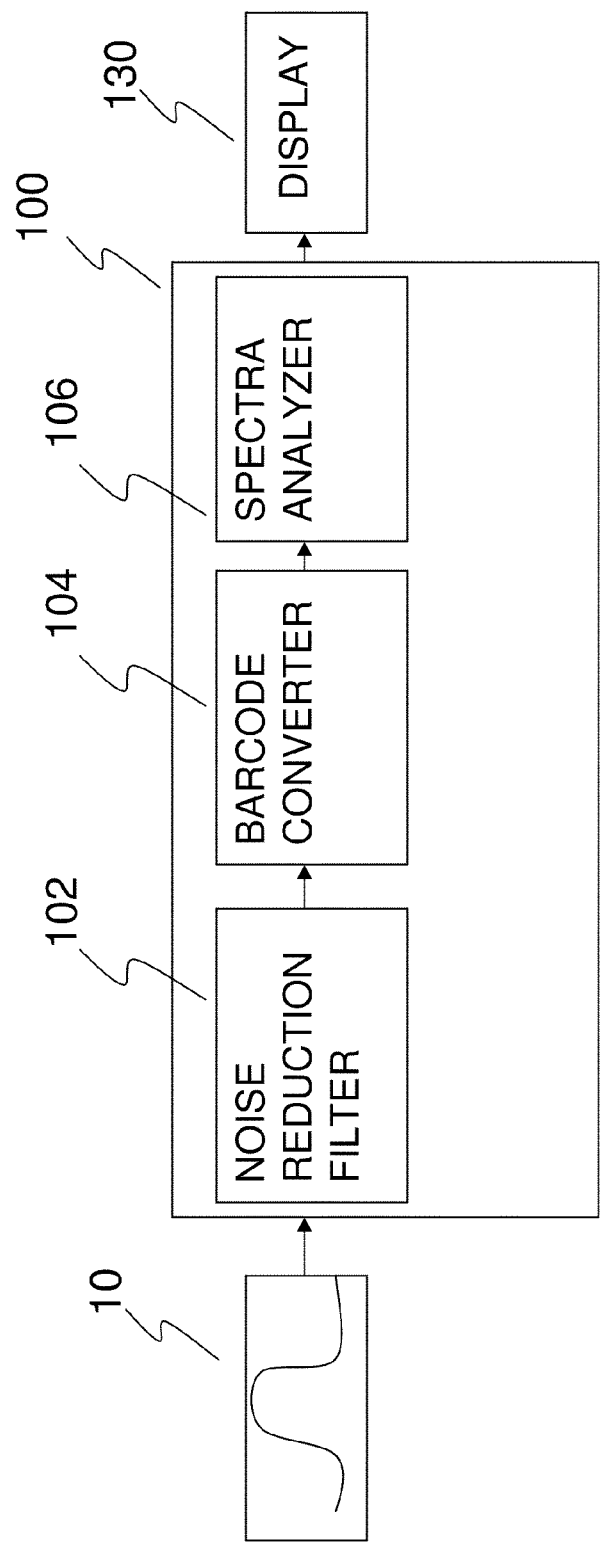
FIG. 1 is a block diagram illustrating the components of an identification system, in accordance with aspects of the invention.

In the following description, specific details are set forth although it should be appreciated by one of ordinary skill that the present invention can be practiced without at least some of the details. In some instances, known features or processes are not described in detail so as not to obscure the present invention.

Multivariate analysis techniques are well-known for reducing a large number of variables to a smaller number of factors for data modeling, and are therefore often used in many standard data and spectral analysis packages. Multivariate analysis techniques can include principal component analysis (PCA), hierarchical cluster analysis (HCA), discriminant function analysis (DFA), and linear discriminant analysis (LDA). One important use of multivariate analysis tools and techniques is to determine in-class or out-of-class membership when relying on a spectrum, for example, a SERS spectrum, of an unknown material to determine its identity. Such materials can include, but not be limited to, viruses, bacteria, microorganisms, pathogens, or other chemical or biological structures, or atomic, molecular, or ionic species thereof. These tools and techniques when combined with library references can form a powerful method for rapid spectroscopic-based identification schemes.

The input for these techniques based on spectroscopic observations typically includes a set of vectors, wherein, in an embodiment, each input vector corresponds to the observed intensity as a function of frequency, e.g., a spectrum. In another embodiment, the input vector corresponds to an intensity as a function of mass. In another embodiment, the input vector corresponds to an intensity as a function of time. Accordingly, the present invention provides variations to input vectors, and more particularly, includes barcodes as input vectors based on each spectrum that is input to an analyzer that performs one or more of the abovementioned multivariate data analysis techniques. The systems and methods introduced by the present invention permit better clustering results to occur as measured by tightly clustered principle component scores, as well as greater separation between clusters of different samples. Hence, observed spectra may be used for more reliable and more specific chemical/biological/material identification.

Embodiments of the present invention feature a spectroscopic-based identification system and method that exploit the enhanced sensitivity offered by SERS, as well as other inputs such as Raman, IR, FTIR, or other spectroscopic inputs, offer for chemical and/or biological material identification, by optimizing robust spectral analysis protocols employing reference library information. Embodiments of the present invention can also be applied to analytical techniques of identification relying on reproducible patterns of input arrays, such as mass spectrometry, chromatography. This is achieved by generating spectral barcodes from the signs of the second derivatives of the spectra of the sample material as a function of frequency; the second derivatives highlighting the shape of the peaks and troughs of the spectra, and derived from the observed spectral intensities as a function of frequency. Thus, each spectrum is reduced to a series of binary values, which are based on whether the second derivatives of the spectrum are greater than or less than zero, i.e., whether the spectrum exhibits up or down curvatures as a function of frequency.

The second derivative-based barcodes are provided as input vectors to a spectra analyzer for cluster analysis such as PCA, and/or DFA, LDA or HCA treatments. Cluster analysis techniques performed on the sign of the second derivative based input spectra can result in clusters that show higher selectivity and improved reproducibility as compared to spectral intensities, or first or second derivative inputs.

Although some embodiments herein refer to methods, it will be appreciated by one skilled in the art that they may also be embodied as a system or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "processor," "device," or "system." Furthermore, aspects of the present invention may take the form of a computer program product embodied in one or more computer readable mediums having computer readable program code embodied thereon.

Any combination of one or more computer readable mediums may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to CDs, DVDs, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowcharts and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

FIG. 1 is a block diagram illustrating the components of an identification system 100, in accordance with aspects of the invention. The identification system 100 comprises a barcode converter 104, a spectra analyzer 106, and an optional noise reduction filter 102.

During operation, a spectrum 10 of a material sample is received by the barcode converter 110. The spectrum 10 can be generated in a manner known to those of ordinary skill in the art, such as Raman spectroscopy, resonance Raman spectroscopy, surface enhanced Raman spectroscopy (SERS), infrared (IR), FTIR, mass spectrometry, or other technique that analyzes reproducible inputs, and to measure the identity, concentration, or amount of a given atomic, molecular, or ionic species corresponding to the inputs. The spectrum 10 includes a plurality of spectral data points from which one or more second derivatives can be determined. Normalized spectra, first derivative spectra, or other types of spectra can also be determined known to those of ordinary skill in the art.

The noise reduction filter 102 can include a Fourier transform processor (not shown) that removes high-frequency noise components from the observed spectrum 10.

Figure 6:
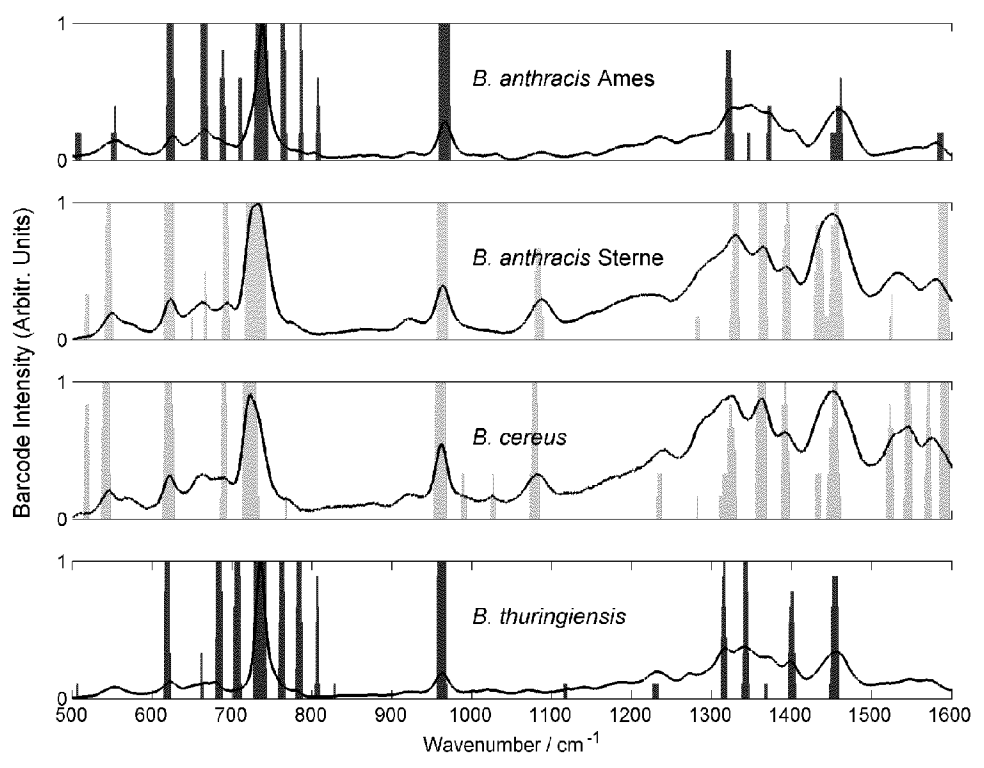

The barcode converter 104 receives at least one second derivative of the spectrum 10. The spectrum includes a plurality of spectral data points, each having a spectral intensity as a function of frequency. The barcode converter 104 includes a processor that generates a second derivative as a function of frequency for each of the spectral data points from its corresponding measured intensity. The barcode converter 104 generates a barcode based on the signs of the second derivatives of the spectrum, shown for example in FIG. 6. In an embodiment, a first barcode value can be assigned for a positive second derivative, for example, binary value "1" corresponding to an upward curvature, and a second barcode value can be assigned for a negative second derivative, for example, binary value "0" corresponding to a downward curvature. In other embodiments, non-binary values can be assigned to form a barcode.

The barcode can be generated from one or more barcode values. When barcodes are generated in this manner, each sample can be uniquely represented by a frequency-dependent binary identification, referred to as a barcode fingerprint.

The second derivative-based barcodes are output from the barcode converter 104 as input vectors to the spectra analyzer 106, which performs barcode spectral data reduction. The spectra analyzer 106 includes a clustering processor, which executes multivariate clustering technique processes for classifying the spectra into correct clusters.

In an embodiment, the spectra analyzer 106 includes a PCA clustering processor (not shown) for performing PCA data reduction. The second derivative-based barcodes are used as input vectors for the PCA data reduction. The principle components (PCs) determined from the barcodes of the unknowns can also be projected into a discriminant function analysis (DFA) space for their identification.

The spectra analyzer 106 can produce and output PCA plots, corresponding HCA dendrograms, or other relevant graphs, plots, or relevant data to a display 130, other external device such as an external processor or analyzer for processing the output from the spectra analyzer 106. The display 130 can include a barcode PCA plot for closely related species or strains, which illustrate clusters corresponding to each chemically distinct sample type derived from the second derivative barcode reduced spectra data that are well-defined and separated from one another.

Figure 2:
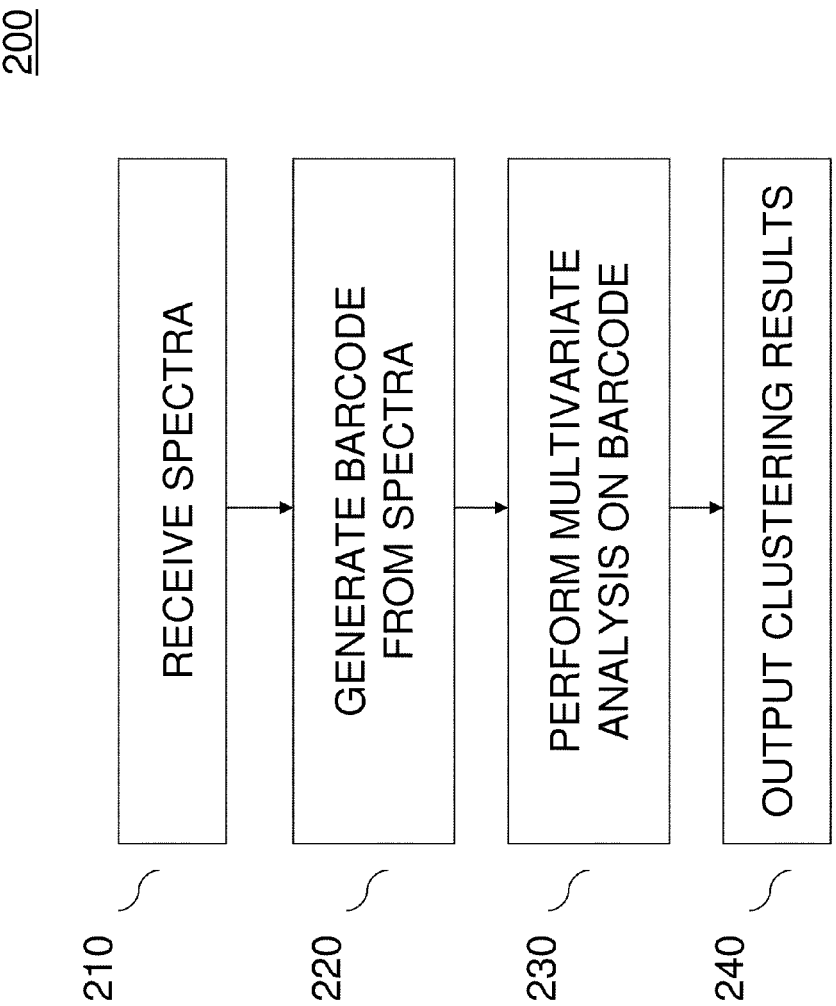
FIG. 2 is a flow diagram of an embodiment of a process for identifying a sample, in accordance with aspects of the invention.
Figure 4:
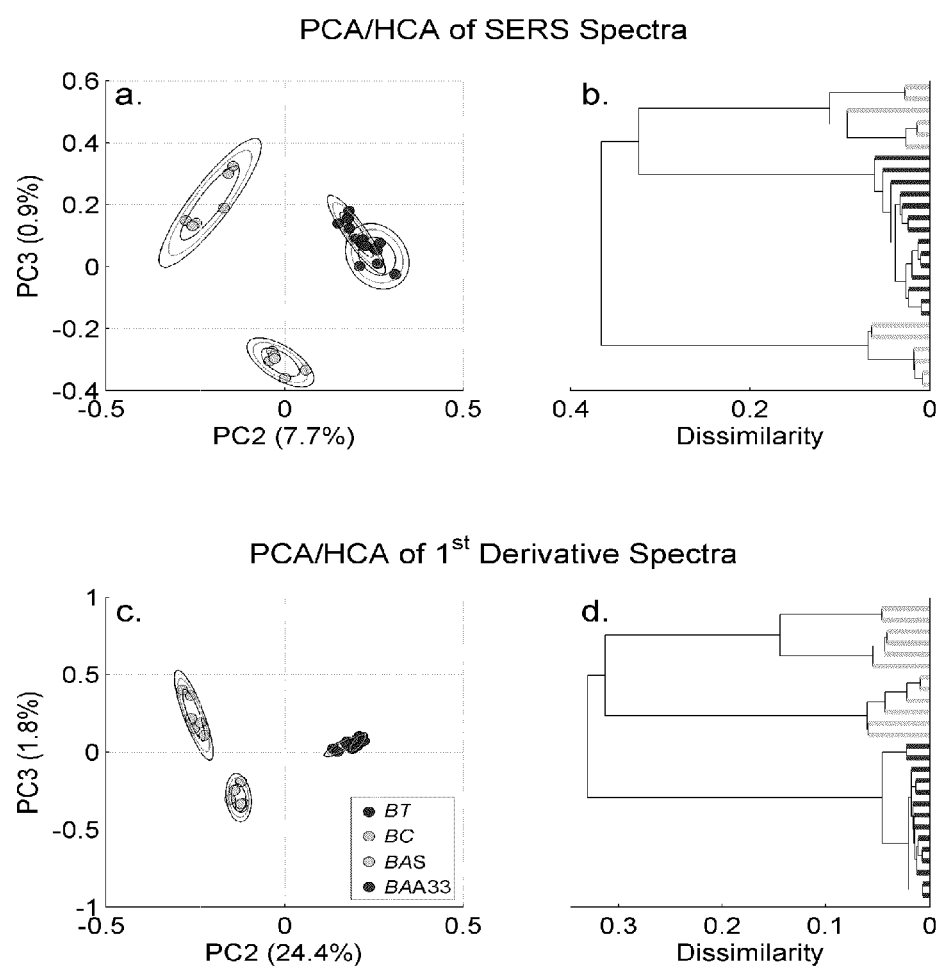
FIG. 4A is a principal component analysis (PCA) plot of PC2 vs PC3 corresponding to the PCA clustering results for the *cereus* group bacterial SERS spectra shown in FIG. 3 based on spectral intensities.
FIG. 4B is a dendrogram corresponding to HCA treatment of PCA clustering results for the *cereus* group bacterial SERS spectra shown in FIGS. 3 and 4A based on spectral intensities.
FIG. 4C is a PCA plot of PC2 vs PC3 corresponding to the PCA clustering results for the *cereus* group bacterial SERS spectra shown in FIG. 3 based on first derivative spectra.
FIG. 4D is a dendrogram corresponding to HCA treatment of PCA clustering results for the *cereus* group bacterial SERS spectra shown in FIGS. 3 and 4C based on first derivative spectra.

FIG. 2 is a flow diagram of an embodiment of a process 200 for identifying a material in a sample, in accordance with aspects of the invention.

According to the process 200, spectra are received (step 210) of the material to be identified. In preferred embodiments, the spectra include second derivatives, also referred to as second derivative spectra. The spectra can be received by an identification system, such as the identification system 100 described with regard to FIG. 1. A Raman or FTIR spectrometer, or other apparatus known to those of ordinary skill in the art, can generate the spectra or input raw data arrays.

In an optional step, high-frequency noise components can be removed from the spectra, for example, using a noise filter that includes a Fourier transform.

One or more barcodes are generated (step 220) from the received spectra. The barcodes are determined from the signs of the second derivatives of the spectra. In an embodiment, a first barcode value can be assigned for a positive second derivative, for example, binary value "1" corresponding to an upward curvature, and a second barcode value can be assigned for a negative second derivative, for example, binary value "0" corresponding to a downward curvature.

A multivariate analysis is performed on the barcodes (step 230). In preferred embodiments, the multivariate analysis includes at least one cluster analysis process, such as PCA. Additional processes such as DFA, HCA, artificial neural network or other multivariate data analysis treatments can also be performed.

Clustering results (step 240) are output in response to the multivariate analysis processes performed on the barcode. The clustering results can be presented to a display or analyzer in the form of a PCA plot, HCA dendrogram, or other analysis tool or technique known to those of ordinary skill in the art.

The present inventive concepts can be used to provide reliable identifications based on input raw data arrays, such as spectroscopic signatures for closely-related raw input data, for example spectra. These inventive concepts are particularly useful for identification schemes based on vibrational spectroscopy. The barcodes generated according to the inventive concepts can provide enhanced identification performance when Raman, FTIR, or SERS is used to distinguish spectra which otherwise appear to be virtually identical via visual inspection.

Thus, the present inventive concepts can be used in applications where there is a need to distinguish Raman, IR spectra, mass spectra, chromatography data, or other observed input data arrays between closely-related samples, and to make an identification. Applications can include, but not be limited to biosensing or bioanalysis, pharmaceuticals, monitoring manufacturing processes, quality control, forensics, DNA sequencing, pathogen detection, medical diagnostics, or food analysis.

One representative application is diagnostic microbiology, for example, bacterial diagnostics, in which the rapid, reliable identification of bacterial pathogens is required. The analysis of corresponding SERS spectra for the detection and identification of bacterial cells with species and strain specificity can be performed according to the present inventive concepts described herein. For example, as shown in illustrative examples described herein, the sign of the second derivative of a surface enhanced Raman spectroscopy (SERS) spectrum can be obtained on in-situ grown gold (Au) cluster covered $SiO_2$ substrates, and a barcode can be generated from the sign of the second derivative, as described in illustrative examples herein. When a multivariate statistical analysis technique such as principal component analysis (PCA) is performed based on the barcode provided thereto as an input vector, improved reproducibility and enhanced specificity can be achieved. For example, the barcode-generated clustering results can be systematically compared to those obtained from corresponding spectral intensities, first derivatives, and second derivatives for the SERS spectra of closely related *cereus* group *Bacillus* strains, described in detail below. PCA plots and corresponding hierarchical cluster analysis (HCA) dendrograms can be generated and displayed that illustrate the improved bacterial identification resulting from the barcode spectral data reduction approach according to the present inventive concepts. As described in the following illustrative example, the identification system and method described herein is critical for the development of SERS microscopy as a rapid, reagentless, portable diagnostic of bacterial pathogens.

It is well-known that the atomistic specificity of vibrational Raman spectral signatures provides a powerful and effective method for chemical identification of both simple molecular species and as well as more complex biological structures. This property, in conjunction with the Raman scattering amplification resulting from the well-known surface enhancement effect observed for molecules in close proximity to nanostructured metal surfaces, has often been exploited for bioanalytical applications, such as glucose level monitoring, viral cell identification, and cancer gene sequence signaling.

A key component of any bacterial diagnostic platform is a data reduction protocol for accurate species/strain identification. Cluster based multivariate data analysis techniques have been exploited previously to demonstrate the potential for SERS and non-SERS Raman alike, as well as FTIR vibrational spectra, to provide unique signatures for bacterial identification. These methods allow the reproducibility and the specificity of a given spectroscopic assay to be quantified and permit the determination of spectral classification within a priori library reference groups. Typically, principal component analysis (PCA) is employed to dramatically reduce the dimensionality of the large spectral arrays, maximize the spectral variances resulting from these input data arrays and provide a basis for subsequent supervised group identification procedures. PCA plots (2D and 3D), and hierarchical cluster analysis (HCA) dendrograms are convenient representations showing naturally occurring group memberships via these objective classification methods. Supervised techniques, such as discriminant function analysis (DFA) or linear discriminant analysis (LDA), which use PC clusters as inputs, have frequently been employed for bacterial identification schemes, particularly for non-SERS Raman analysis. Model training techniques based on genetic algorithm or artificial neural network approaches have been used much less frequently for vibrational bacterial specificity analysis.

As a further additional step toward evaluating the performance of the abovementioned substrate for use in a SERS based or non-SERS based bacterial diagnostic platform, a method as described herein provides for bacterial identification via PCA, HCA or DFA multivariate statistical analyses. The following illustrative example describes a second derivative-based clustering approach in accordance with embodiments of the present inventive concepts, combined with the reproducibility provided by the in situ grown Au nanoparticle covered substrates, which results in excellent species and strain level clusters for bacterial identification in a group of closely related bacteria. Such a quantitative treatment also allows the diagnostic capabilities resulting from different SERS substrates to be compared.

In this example, analysis of the SERS spectra of members of the cereus group of Bacillus bacteria, in particular B. anthracis (Sterne and Ames), B. thuriengensis and B. cereus is provided. In contrast to the often lethal consequences in humans resulting from infections with *B. anthracis, B. cereus* is a commonly found soil bacterium that can result in food poisoning and *B. thuringiensis* produces a protein toxic to insect larvae and is thus widely used as a biological pesticide. The capability of distinguishing between avirulent *B. anthracis* strains; *B. anthracis* Sterne, and *B. anthracis* Ames, and the genetically closely related *B. cereus* and *B. thuringiensis* species is demonstrated. Despite the range of pathological effects manifested by these bacteria, genetic evidence has been used to argue that these organisms constitute a single species, attesting to the similarity and phylogenic proximity of these species. Thus, the ability to rapidly distinguish between these organisms, as well as between strains within this group, is a minimum requirement for bacterial diagnostic testing for the causative agent of anthrax and can serve as a good test of the SERS specificity resulting from the Au nanostructured substrates and the multivariate data processing protocols employed here.

A clustering analysis is also performed to introduce a crucial attribute of Raman spectroscopy, for example, SERS, as compared to other optical approaches for bacterial identification. Based on observed spectral differences, it has been demonstrated that the spectral distinction between bacterial species derived from FTIR and normal Raman spectra is generally much smaller than the specificity obtained from SERS vibrational signatures. This effect is fundamentally attributable to the distance dependence of the mechanisms for SERS activity. Thus, PC cluster bacterial identification methods based on SERS spectra can exhibit enhanced specificity, as well as sensitivity, compared to FTIR or normal Raman spectra fingerprinting schemes. This additional important advantage of SERS for bacterial diagnostics is readily demonstrated by use of the clustering analysis described here and serves to highlight the effectiveness of SERS for microorganism detection and identification via optical approaches.

Embodiments of the present inventive concepts include the use of bacterial strains, their sources and additional relevant genotypic descriptions. A summary of such bacterial strains investigated by SERS is described in Table 1. The bacterial strains are grown in ~15 mL of LB (Sigma) broth, harvested during the log growth phase by centrifugation and washed five times with deionized Millipore water. The resulting cell pellet is resuspended in 0.25 mL of water and 1 μL of the resulting ~$10^9$/mL bacterial suspension is pipeted directly onto the SERS substrate for purposes of the data analysis described herein. SERS measurements are made after about two minutes when nearly all the water has evaporated. Signal acquisition during this one to two minute period results in variable SERS signal intensities due to bacterial mobility and reduced bacteria-substrate surface interactions. In order to obtain non-SERS Raman spectra of bulk bacterial samples, bacteria can be placed on KBr plates.

TABLE 1

| Species | Strain ID | Relevant Genotype |
|---|---|---|
| *Bacillus thuringiensis* | ATCC 35646 | Wild-type environmental isolate |
| *Bacillus cereus* | ADL#830 | Strain T, wild-type prototrophic |
| *Bacillus anthracis* | Sterne | $pXO2^-$ |
| *Bacillus anthracis* | Ames 33 | $pXO1^-$ $pXO2^-$ |
| *Bacillus anthracis* | Ames 35 | $pXO2^-$ |
| *Bacillus licheniformis* | ATTC 9945 | Wild-type environmental isolate |
| *Mycobacterium smegmatis* | ATCC 35797 | Wild-type strain 1717 |
| *Mycobacterium fortuitum* | ATCC 35754 | TMC 1530; clinical isolate from human sputum |
| *Escherichia coli* | ATCC 12435 | A lambda-derivative of *E. coli* laboratory strain K-12 |
| *Salmonella typhimurium* | ATCC 14028 | Wild-type isolated from animal tissue |

All SERS spectra shown in this example were obtained using the in-situ grown, aggregated Au nanoparticle covered $SiO_2$ substrate. A two stage reduction of a metal doped sol-gel results in small (2-15 particles) aggregates of monodispersed ~80 nm Au nanoparticles covering the outer layer of ~1 $mm^2$ $SiO_2$ substrate. The slowest step in this production scheme is the second reduction step in very dilute $NaBH_4$ which requires about 24 hours for the in situ growth of the Au nanoparticle clusters. The shelf life of these sol-gel based substrates is currently in excess of 90 days. Thus, the SERS substrate combines attributes of the chemically produced colloids which result in large enhancement factors ($10^4$-$10^5$ per bacterium) with solid state ease of use and reproducibility.

The spectra described in this example are acquired with a RM-2000 Renishaw Raman microscope employing a 50× objective and excited at 785 nm. SERS spectra are obtained with incident laser powers in the 1-3 mw range in ~10 seconds of illumination time. The observed spectra results from ~10-20 bacterial cells within the field of view (~100 $\mu m^2$). Spectral resolution is set to 3 $cm^{-1}$, although the minimum width for an observed bacterial spectral feature is 5 $cm^{-1}$ (FWHH). The 520 $cm^{-1}$ band of a silicon wafer was used for frequency calibration. Non-SERS spectra of bacteria is acquired with 60 seconds of 300 mw of incident 785 nm power.

Initially, an automated curvature-based procedure can be applied to eliminate spurious cosmic ray contributions to the SERS spectral signatures. For purposes of bacterial identification, all SERS spectra is subsequently Fourier filtered to remove high frequency noise components from the observed spectra. The multivariate data analysis is carried out with MatLab™ software subroutines. Principal component analysis (PCA) is performed on normalized spectra, first derivative spectra and second derivative spectra in the 500 cm$^{-1}$ to 1600 cm$^{-1}$ range. Input arrays are splined to 1 intensity value per cm$^{-1}$. In another cluster method, binary barcodes based on the sign of the second derivative of the spectrum are generated as input to the PCA clustering algorithms. A minimum value, typically at ~10% of the maximum second derivative value, can be used as a threshold for the zero (one) assignment. This cutoff value can be determined empirically and used without change throughout these studies. Mean centering the input spectral data does not affect the outcome of the clustering results described here. The PCA reduced data sets can be used as inputs to hierarchical cluster analysis (HCA) procedures. Both Ward's algorithm and squared distances can be used to evaluate the member dissimilarity for the HCA procedure. HCA results were summarized by corresponding dendrograms. Dendrograms can be constructed using member distances directly in order to display the large dynamic range of branching points resulting from the branching of the well separated tightly packed groups. The resulting principal components can be inputs to a discriminant function analysis (DFA) as well. The Discriminant Partial Least Squares 2 (DPLS2) algorithm can be used in creating the discriminant functions. Since the DFA space results from a rotation of the selected PCA subspace, each DF is simply a linear combination of these inputed PCs. Only the PCs carrying the most significant variance of a given data set, typically up to 98%, is used in the DFA treatments discussed herein.

Figure 3:
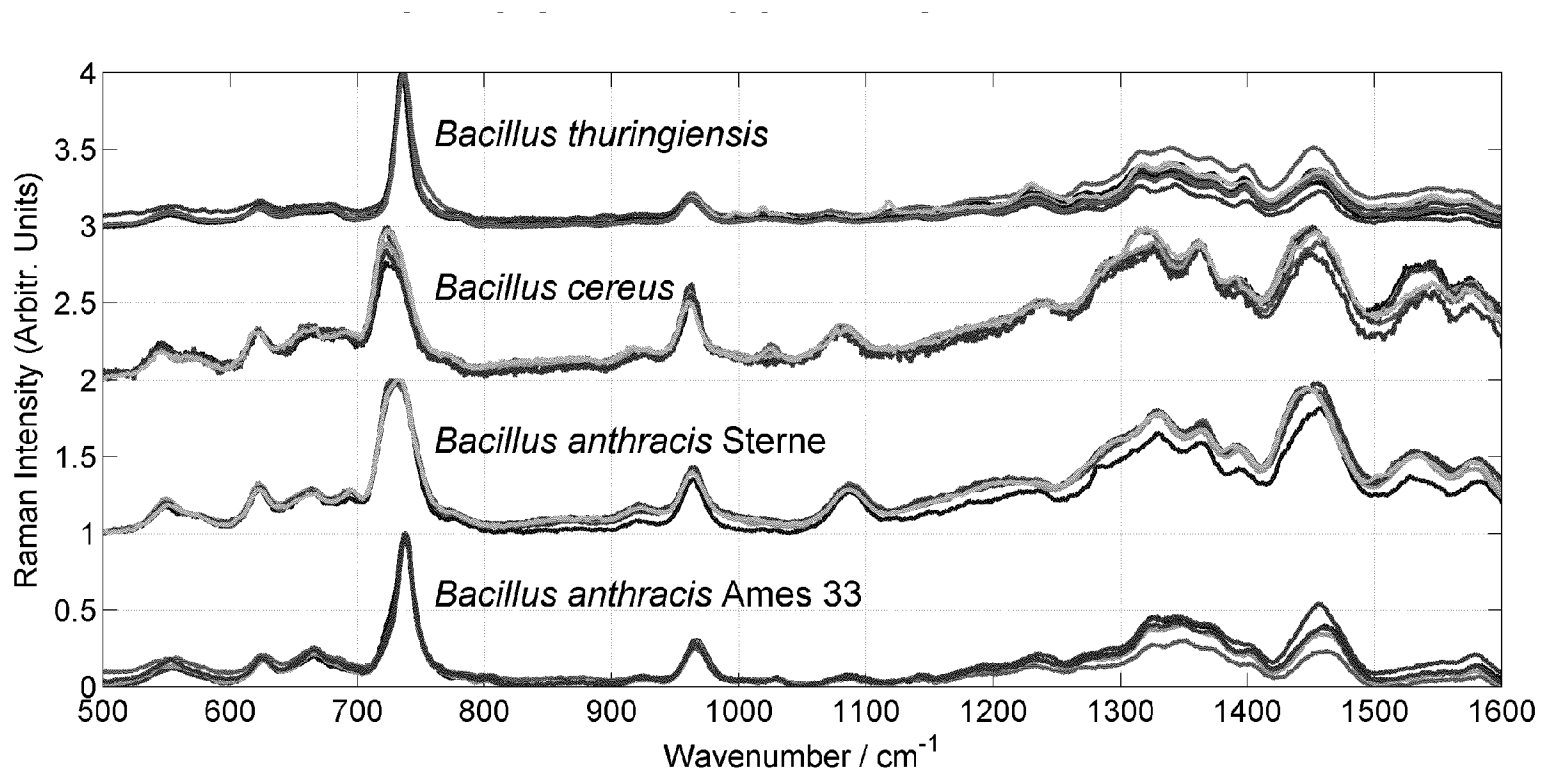
Figure 5:
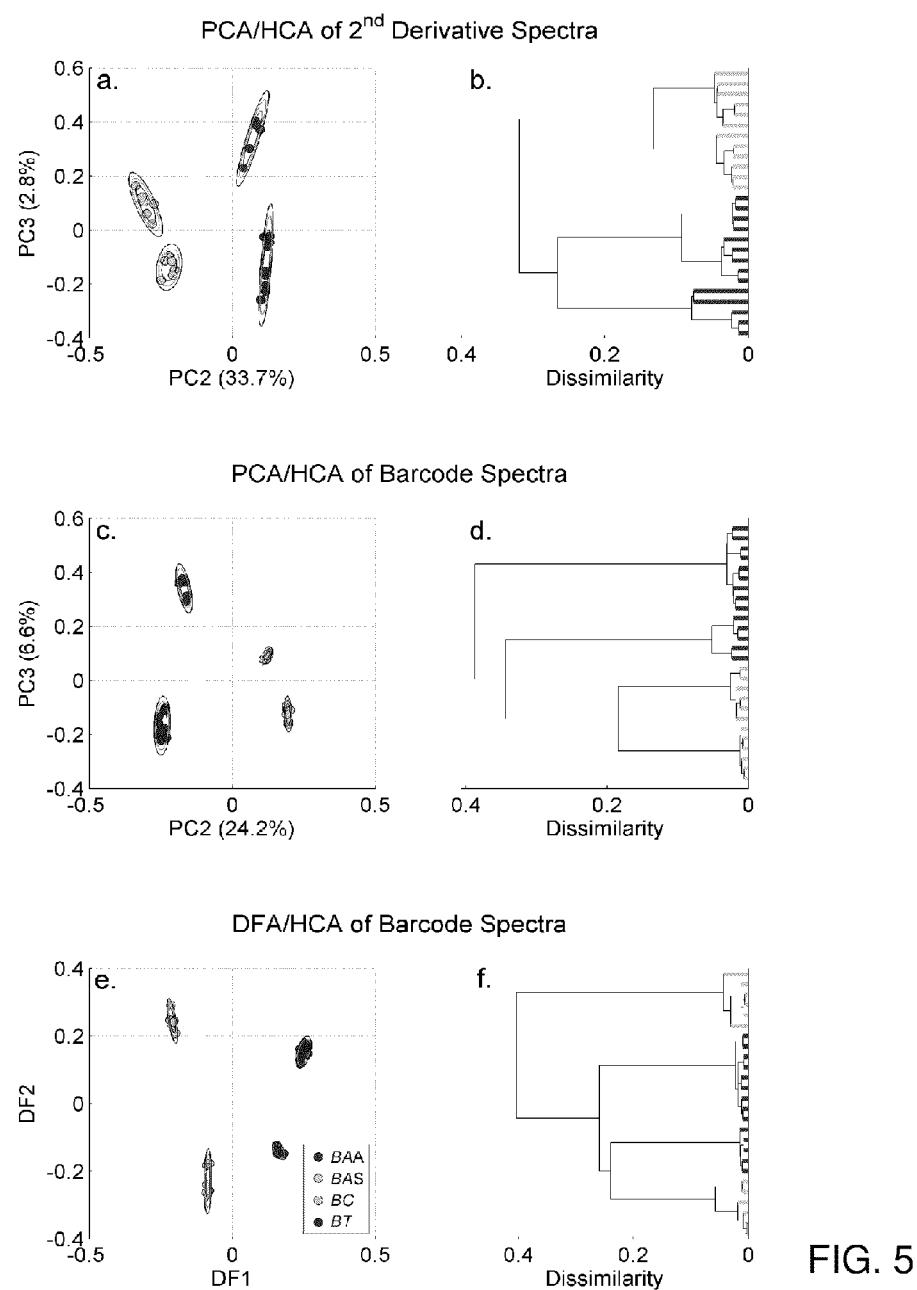
FIG. 5A is a PCA plot of PC2 vs PC3 corresponding to the PCA clustering results for the *cereus* group bacterial SERS spectra shown in FIG. 3 based on second derivative spectra.
FIG. 5B is a dendrogram corresponding to HCA treatment of PCA clustering results for the *cereus* group bacterial SERS spectra shown in FIGS. 3 and 5A based on second derivative spectra.
FIG. 5C is a PCA plot of PC2 vs PC3 corresponding to the PCA clustering results for the *cereus* group bacterial SERS spectra shown in FIG. 3 based on second derivative-based barcodes.
FIG. 5D is a dendrogram corresponding to HCA treatment of PCA clustering results for the *cereus* group bacterial SERS spectra shown in FIGS. 3 and 5C based on second derivative-based barcodes.
FIG. 5E is a discriminant function analysis (DFA) plot corresponding to barcode treatment of *cereus* group SERS data.
FIG. 5F is an HCA dendrogram corresponding to barcode treatment of *cereus* group SERS data shown in FIG. 5E.

FIG. 3 is a graph illustrating SERS spectra of four members of a group of bacteria. In particular, multiple SERS spectra of four strains of the *cereus* group of *Bacillus* bacteria, *B. anthracis* Sterne, *B. anthracis* Ames 33, *B. cereus* and *B. thuringiensis*, in the 500 $cm^{-1}$ to 1600 $cm^{-1}$ range, normalized by the largest spectral intensity of each spectrum, are shown. The degree of spectral (intensity, frequency and band shape) variability for a given species due to both SERS substrate and the bacterial cell in homogeneities, is evident in FIG. 3. Spectra for a given species is acquired on different in situ grown Au nanoparticle covered $SiO_2$ substrates for a given isolate. SERS spectra of bacteria on the gold nanoparticle covered substrates can exhibit very similar and often analogous spectral features, such as the strong bands at ~730 $cm^{-1}$, 960 $cm^{-1}$, 1090 $cm^{-1}$, and 1450 $cm^{-1}$. The pattern of these vibrational bands is qualitatively similar in all the SERS spectra of these closely related *cereus* group bacteria and constitutes a rigorous test of multivariate data reduction methods for species/strain specific bacterial diagnosis. The SERS spectra of *B. anthracis* Sterne and *B. cereus* appear to be nearly homologous while the *B. thuringiensis* and *B. anthracis* Ames 33 SERS spectra appear to be similar. The empirical differences between the two *anthracis* strains (Ames 33 and Sterne) SERS spectra are more evident than those between the SERS spectra of different species within the set of spectral data shown in FIG. 3. Much of *B. anthracis* virulence is extracellular and is controlled by genes on two plasmids, pX01, i.e., encoding the secreted proteins protective antigen, lethal factor end endema factor, and pX02, i.e., encoding the cell surface poly-D-glutamic acid capsule. As summarized in Table 1, the two *B. anthracis* strains described herein each contain different complements of the two virulence plasmids.

A series of PCA plots and corresponding HCA dendrograms, resulting from different treatments of the *cereus* group SERS spectra shown in FIG. 3 are compared in FIGS. 4A-4D and 5A-5D. Each cluster ring in FIG. 4 represents a two dimensional standard deviation. For all the PCA results shown, PC3 vs. PC2 is plotted. This is generally the 2D contour in PC space that exhibits the greatest cluster separation at the highest level of significance. The percent variance captured by each of these principal components is indicated in parenthesis along the corresponding PCA axis. In addition, for each clustered species, three two-dimensional Gaussians are drawn centered on the average value of a clustered group. Each resulting ellipse corresponds to a standard deviation for the PCA values of that distribution. Each cluster ring represents a two dimensional standard deviation. These rings are a representation of the reproducibility of the data and offer a quantitative measure of the significance of the distance between clusters of different species/strains. Such standard deviation rings can be used as one measure of the diagnostic specificity offered by different substrates or alternative multivariate clustering strategies.

As evident in the PC3 vs. PC2 plots shown in FIGS. 4A-4D, the PCA analysis based on the normalized spectral intensities (FIG. 4A) or the first derivative (FIG. 4C) of the SERS spectra of these four strains show well-separated distinct *B. anthracis* Sterne and *B. cereus* clusters, but *B. anthracis* Ames 33 and *B. thuringiensis* are substantially overlapped. The corresponding distance based HCA dendrograms (FIGS. 4B and 4D) convey this same assignment difficulty in the grouping of the *B. anthracis* Ames 33 and *B. thuringiensis* for the SERS spectra of the intensity and first derivative spectra. Ames 33 and *thuringiensis* cannot be separately classified in these HCA dendrograms. As described above, within this data set the two *B. anthracis* strains (Ames 33 and Sterne) are judged to be more distinct than the *B. anthracis* Ames and *B. thuringiensis* species on the basis of these SERS fingerprints. The results imply that that the latter pair shares a greater similarity of cell surface features than does the former pair of strains.

In contrast, when the SERS spectra second derivatives, which highlight the shape of the peaks and troughs of the spectra, are used as input vectors for the correlation coefficients of the PCA treatment, improved cluster separation is obtained for this group of species in the PC2 vs. PC3 plane, as shown in FIG. 5A. Further clarity with regard to the correct identification grouping of these spectra is evident in the corresponding HCA dendrogram (FIG. 5B) as well. Thus, the shape of the peaks and valleys of this SERS signature can offer a more bacteria-specific fingerprint than that due to either the peak intensities or slopes of the spectral features shown in FIG. 4.

Improved clustering results derived from the SERS bacterial spectra are consistently obtained when second derivative-based barcodes are used as input vectors for the PCA treatment, for example, shown in FIG. 5C. As described above, when barcodes are assigned on the basis of the second derivative sign, i.e. +1 for upward curvature, (positive second derivatives) and 0 for downward curvature (negative second derivatives), each species is represented by a frequency dependent binary fingerprint. A threshold for zero, usually set at about 10% of the maximum value of the second derivative, is used to determine a minimum value for a 0 bit assignment for this barcode. This threshold helps discriminate against residual noise components.

FIG. 6 is a graph illustrating averaged barcodes derived from the SERS spectra of FIG. 3 for each bacteria sample, in accordance with aspects of the invention. In particular, FIG. 6 shows second derivative barcodes for the abovementioned four *Bacillus* species of interest. For second derivatives $<0.007$, the array spectral point is assigned a value of +1; otherwise the array point is 0 for the shown barcode. Averaged spectra are overlaid with the corresponding barcode.

As seen in FIG. 6, averaged barcodes for each of the species of interest here exhibit a unique SERS based signature. The resulting barcode PCA plot for these closely related *Bacillus* strains is shown in FIG. 5C. PC clusters corresponding to each of the four *Cereus* group bacteria derived from the second derivative barcode reduced SERS spectra data are well defined and separated from one another. The intragroup distances are minimized and the intergroup separations are maximized via this barcode PCA treatment relative to intensity, first or second derivative-based PCA results, as shown in the comparison between FIGS. 4A, 4C, 5A, and 5C. Furthermore, the two-dimensional Gaussian contours shown in FIG. 5C reveal that many standard deviations (>10) separate the four species in the barcode based PCA plot (FIG. 5C). In an alternative display of the specificity afforded by this barcode approach normalized spectra, normalized first and second derivative spectra and barcodes of the four *Bacillus* strains were subject to a PCA clustering treatment. In this normalized data test the barcode-reduced SERS spectra are shown to provide widely separated classification clusters at the highest levels of significance as compared to comparably normalized spectra or derivative spectra.

A dendrogram derived from HCA calculations (FIG. 5D) also illustrates the success of this barcode approach as compared to the clustering derived from intensity, first derivative or second derivative-based spectra (FIGS. 4B, 4D, 5B, 5D). Not only are all the spectra properly classified according to species/strain in the barcode based HCA dendrogram (FIG. 5D), but the branching point for the members of a given species/strain type consistently occurs at smaller dissimilarity scores while the dissimilarity score is a maximum for the different strains in this dendrogram as compared to the other PCA derived dendrograms for this same initial set of SERS spectra (FIGS. 4B, 4D, 5B, 5D). The HCA dedrograms given here are based on distances in the PC3 vs. PC2 plane only. However, more dimensions (up to the PC dimensionality) could in principle be used to construct dendrograms for identification purposes. Using a convenient unsupervised strategy, all the PCs weighted by their significance are used to construct dendrograms for the data sets employed here. Due to the relatively small number of groups (4) and the quality of the PC3 vs. PC2 clustering results, the weighted PC dendrogram do not result in superior cluster differentiation for the data sets considered herein.

The PCA generated clusters can be employed in a supervised classification software program. The results of a discriminant function analysis (DFA) based on PCs derived in the barcode clustering procedure are shown in FIG. 5E. Only the PCs of greatest significance were retained for this DF1 vs. DF2 plot. For the data shown here, these discriminant functions consisted of linear combinations of the first five PCs and were dominated by the contribution of a single PC. Due to the high quality of the unsupervised PCA results, only a very modest improvement in the cluster grouping is seen in the resulting DFA results. Species/strain cluster separation is slightly larger in the DFA plot (FIG. 5E) than in the corresponding PCA result (FIG. 5C) and the dissimilarity scores are nearly all smaller in the HCA dendrograms derived from the DFA results (FIG. 5F) as compared to the corresponding PCA and/or HCA results (FIG. 5D).

Figure 7:
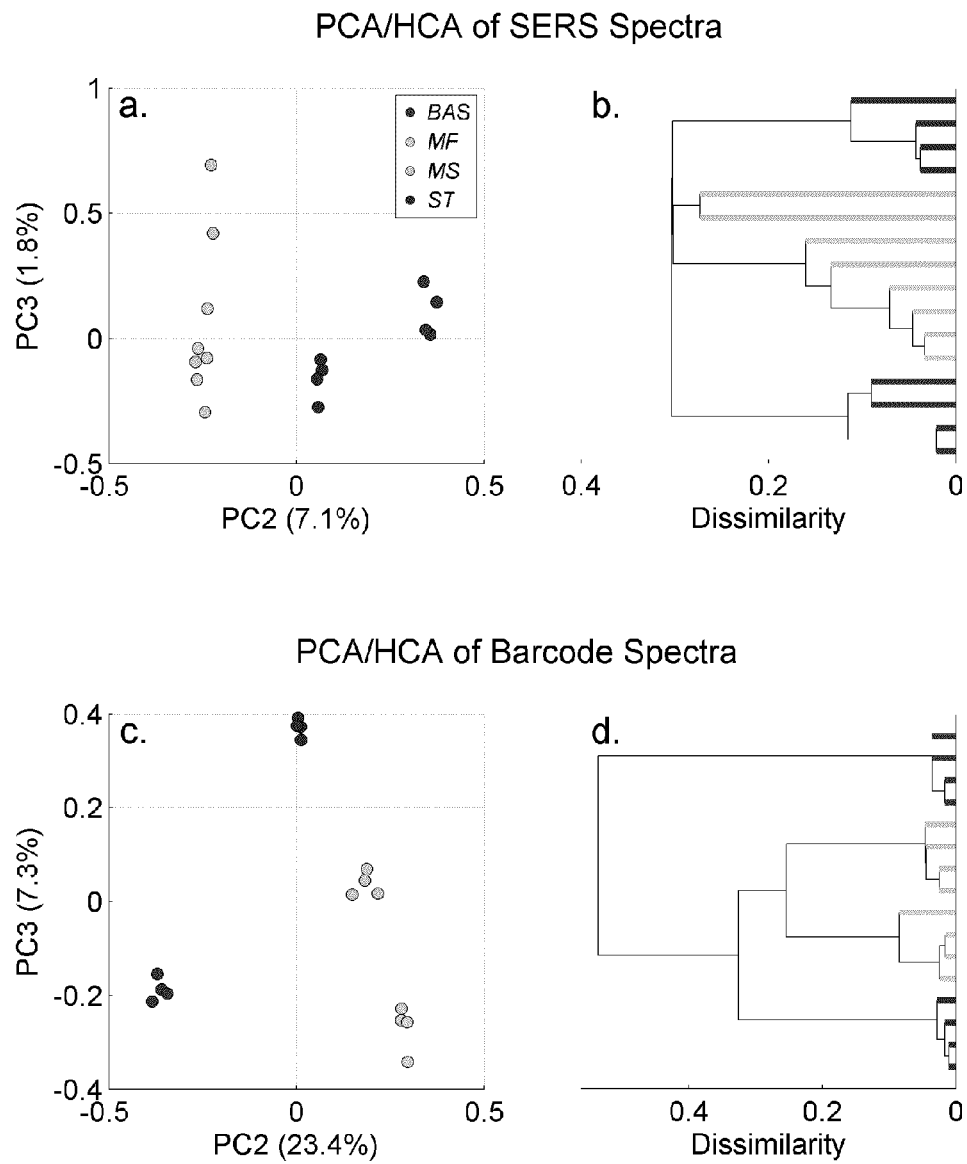
FIG. 7A is a PCA plot for SERS spectra of *Bacillus anthracis* Sterne, *Mycobacterium fortuitum, Mycobacterium smegmatis* and *Salmonella typhimurium*.
FIG. 7B is an HCA dendrogram corresponding to the PCA plot shown in FIG. 7A.
FIG. 7C is a PCA plot for a second derivative barcode representation of the SERS spectra of FIG. 7A.
FIG. 7D is an HCA dendrogram corresponding to the PCA plot shown in FIG. 7C.

The specificity and reproducibility that typically results from the use of the barcode representation of the SERS bacterial data acquired on the gold nanoparticle covered substrates is additionally demonstrated in FIG. 7. A PCA plot of SERS spectra and the corresponding second derivative barcode representation of the SERS spectra are contrasted in this figure for four bacterial species; *M. fortuitum, M. smegmatis, S. typhimurium* and *B. anthracis* Sterne. The dramatically improved clustering and interspecies cluster distance enhancement resulting from the use of the barcode treatment of the SERS data is evident in this figure (compare FIGS. 7A and B with FIGS. 7C and D). These results and the more extensively described *Cereus* group analysis described above, are typical for the SERS bacterial spectra acquired on the gold nanocluster covered SERS substrates and thus indicate that a PCA/DFA scheme based on the barcode reduced SERS signatures provides the best analysis protocol for bacterial identification, at least compared to the other input vector strategies described herein.

Figure 8:
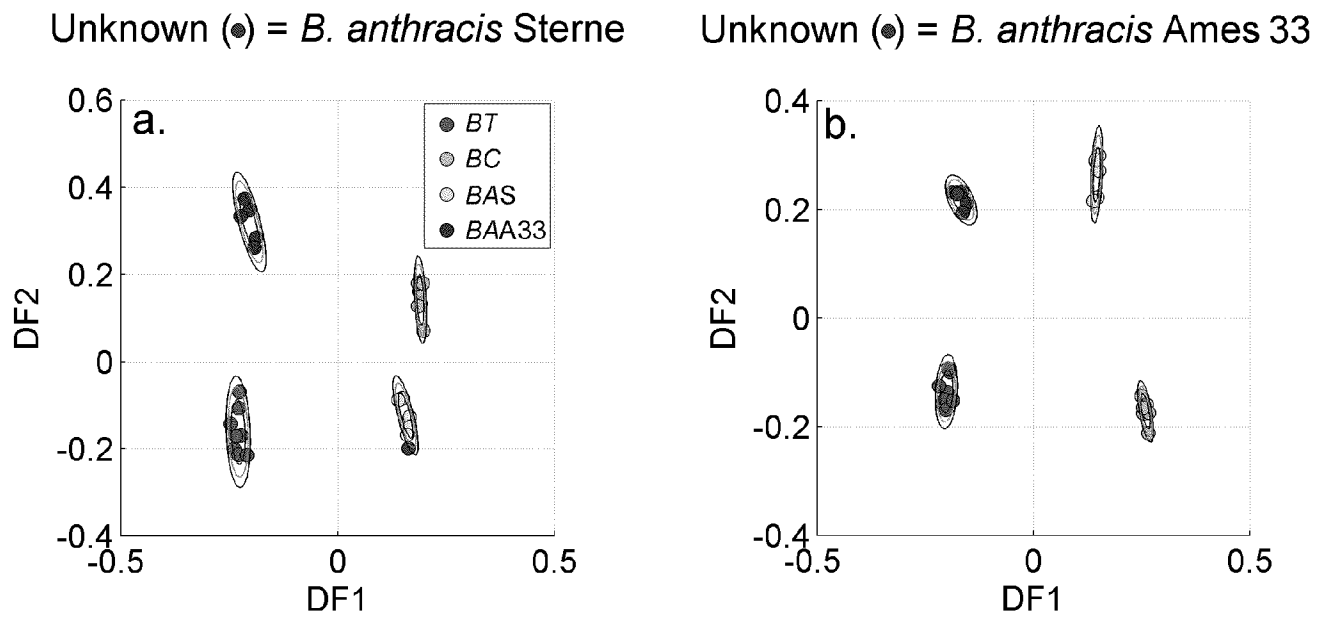

Given the high quality of the PCA-DFA plots based on the second derivative sign, the identification of in-class membership demonstrated with a leave-one-out strategy employing the PCA or DFA vectors derived from the barcode data training set is virtually assured for the SERS data shown in FIG. 14. Two examples of positive identification using a *B. anthracis* Ames 33 and a *B. anthracis* Sterne SERS spectrum are demonstrated by the results shown in FIG. 8. DFA training sets derived from the n-1 spectral signatures are given in FIGS. 8A and B, wherein n is the total number of spectra in FIG. 3. The above-described second derivative-based barcodes are used as input vectors for the PCA data reduction. When the PCs determined from the barcodes of the unknowns are projected into the DFA space they each fall in the correct *Bacillus anthracis* strain cluster for their identification. Note that the DFA plots are slightly different for these two examples (FIGS. 8A and 8B) because the training sets differ by one member.

Figure 9:
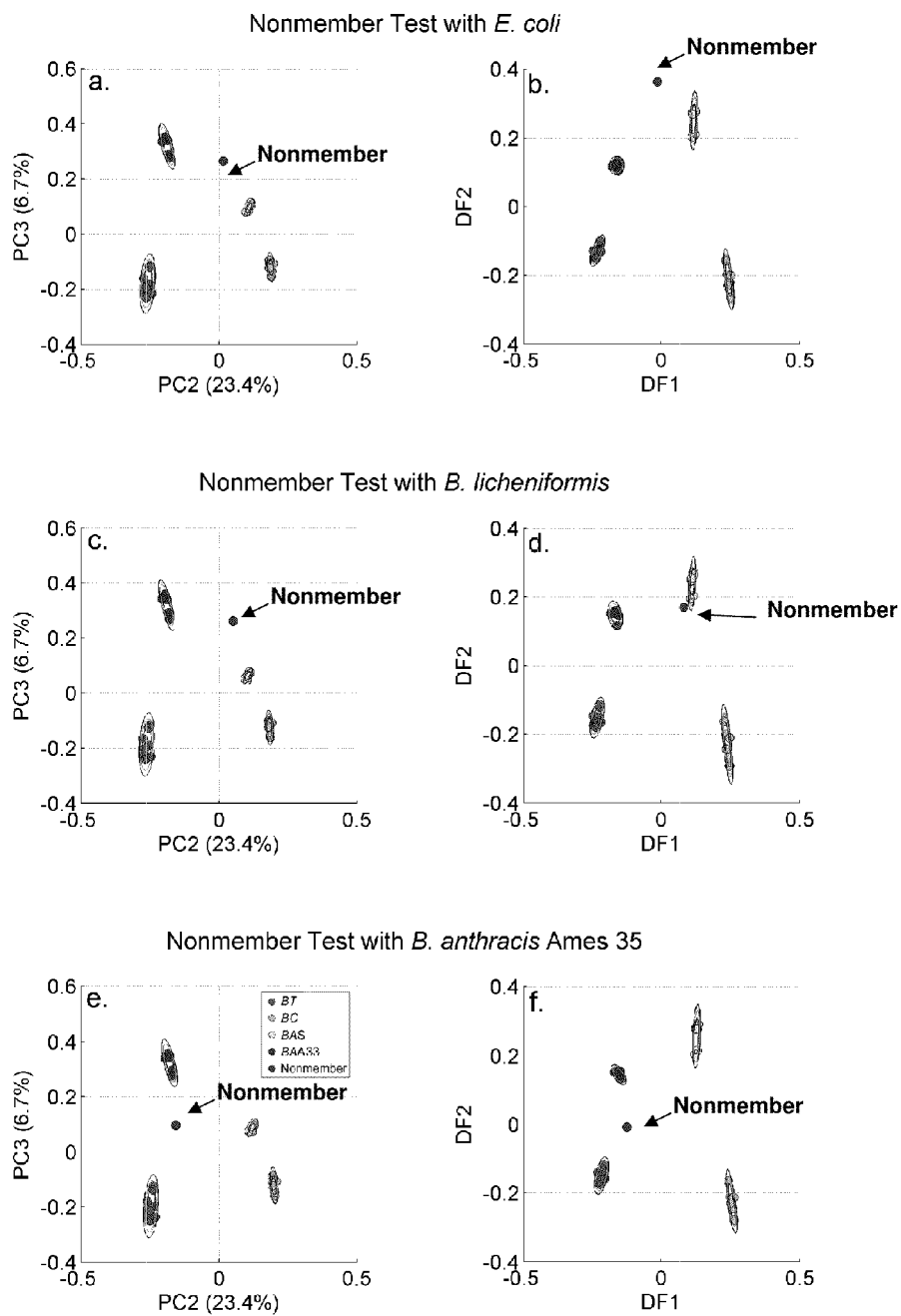
FIG. 9A is a barcode-based PCA plot of an out-of-group unknown.
FIG. 9B is a barcode-based DFA plot of the out-of-group known of FIG. 9A.
FIG. 9C is a barcode-based PCA plot of another out-of-group unknown.
FIG. 9D is a barcode-based DFA plot of the out-of-group known of FIG. 9C.
FIG. 9E is a barcode-based PCA plot of another out-of-group unknown.
FIG. 9F is a barcode-based DFA plot of the out-of-group known of FIG. 9E.

A more rigorous test of this clustering based procedure for bacterial identification can be the ability to discriminate against out-of-class species or false positive bacterial classifications. Avoiding such misclassifications is just as significant for the success of an identification scheme as a correct positive identification grouping. In FIG. 9, the ability of the PCA and DFA *cereus* group clustering results discussed above to discriminate are compared and contrasted against 3 different out-of-class unknowns: *E. coli, B. licheniformis* and *B. anthracis* Ames 35. This group tests the ability of the PCA/DFA clusters of *B. anthracis* Sterne, *B. anthracis* Ames 33, *B. cereus* and *B. thuringiensis* to demonstrate out-of-class or non-members from another genus, the same genus and another closely related strain. In FIGS. 9A, 9C, and 9E, the PCA PC2 vs. PC3 plots are shown resulting from inclusion of each of these unknowns: *E. coli, B. licheniformis* and *B. anthracis* Ames 35, respectively. In each case the unknown does not find a match with any of the known clusters displayed. The unknowns are more than 10 standard deviations away from any group cluster mean coordinates for these PCA contours. Interestingly, the Ames 35 SERS spectrum has the same PC3 value as Sterne but the same PC2 as Ames 33 (FIG. 9E). Ames 35 is a descendent of the Ames genotype but is missing the same virulence plasmids as Sterne does (see Table 1). The PCA SERS plot for this strain seems to reflect these genetic factors.

In FIGS. 9B, 9D, and 9F, the results of projecting the PCs for the unknown into the DFs generated by the training set that does not include the unknown, are displayed in DF1 vs. DF2 plots. The most significant observations is that the *B. licheniformis* spectrum nearly clusters with the *B. anthracis* Sterne grouping (FIG. 9D). The DFA vectors which are linear combinations of the selected PCs, have been determined in order to maximize the distance between different groups and minimize the distance between intragroup members. In contrast, the unsupervised PCA treatment maximizes the variance between all the members of the input data set. Consequently, the rotation of PCs that results in DFs, may coincidently result in a linear combination of PCs that locates an unknown in an incorrect cluster. Clustering that is dependent on supervised methods such as DFA in order to achieve reliable specificity runs the risk of false positive identifications as shown here. Thus, unsupervised multivariate approaches which result in well-clustered groupings seems to offer the best chance for avoiding potential false positive identifications.

Having established the specificity afforded by the barcode reduction of SERS spectra for multivariate data analysis, this approach can highlight an essential attribute of SERS for microorganisms identification. Aside from the advantages resulting from the Raman cross section enhancement, such as reduced data collection time, single cell level sensitivity and reduced incident laser power requirements, thus enabling portable and remote (SERS) Raman detection instrumentation, a somewhat more subtle but important attribute for bacterial identification derives essentially from the distance and orientation dependence of the SERS enhancement mechanisms. As previously described, SERS spectra of *E. coli* and *S. typhimurium* can be more spectrally distinct than their corresponding nonSERS (bulk) Raman spectra based on qualitative spectral comparison and first derivative difference spectra. Non-SERS or bulk Raman spectra of bacterial species often exhibit only very subtle spectral differences even for bacteria from different genera although these distinction can be discerned in PCA analysis.

Figure 10:
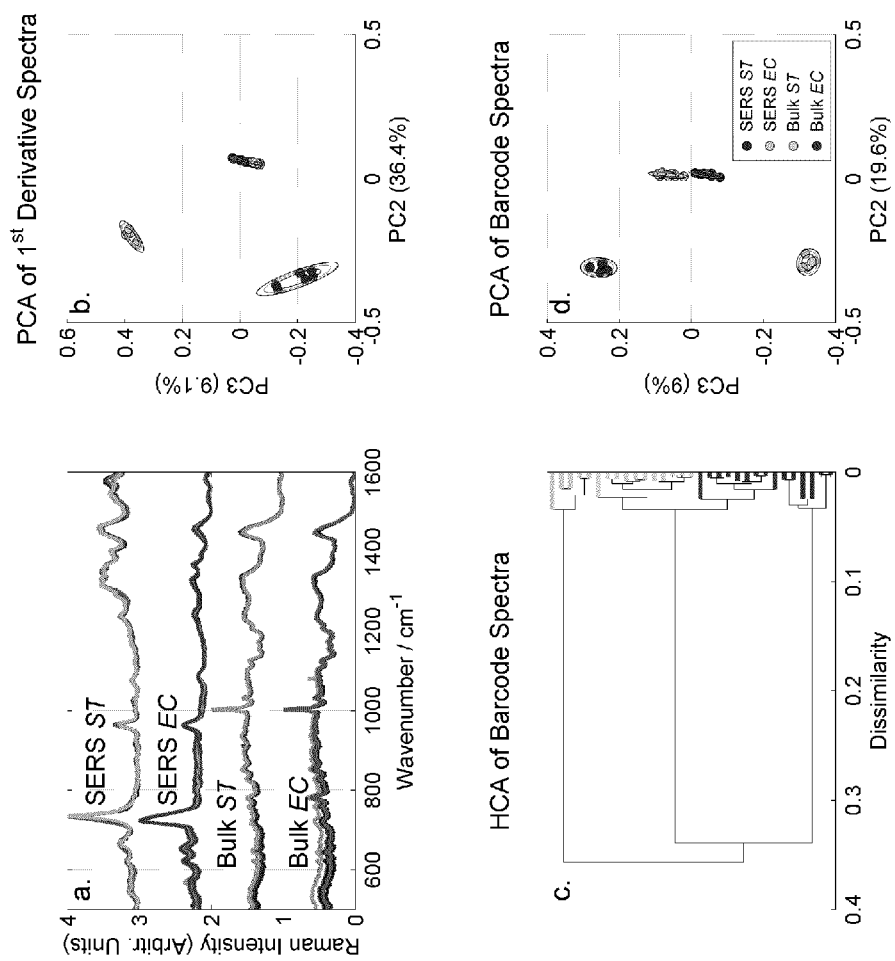
FIG. 10A is a graph illustrating SERS and non-SERS bulk spectra of *S. typhimurium* (ST) and *E. coli* (EC).
FIG. 10B is a PCA plot of the corresponding first derivative SERS and non-SERS spectra of *S. typhimurium* (ST) and *E. coli* (EC).
FIG. 10C is an HCA dendrogram of SERS and non-SERS PCA clusters resulting from the barcode treatment of the spectra shown in FIG. 10A.
FIG. 10D is a PCA barcode clustering of SERS and bulk ST and EC spectra corresponding to FIGS. 11A-11C.
Figure 11:
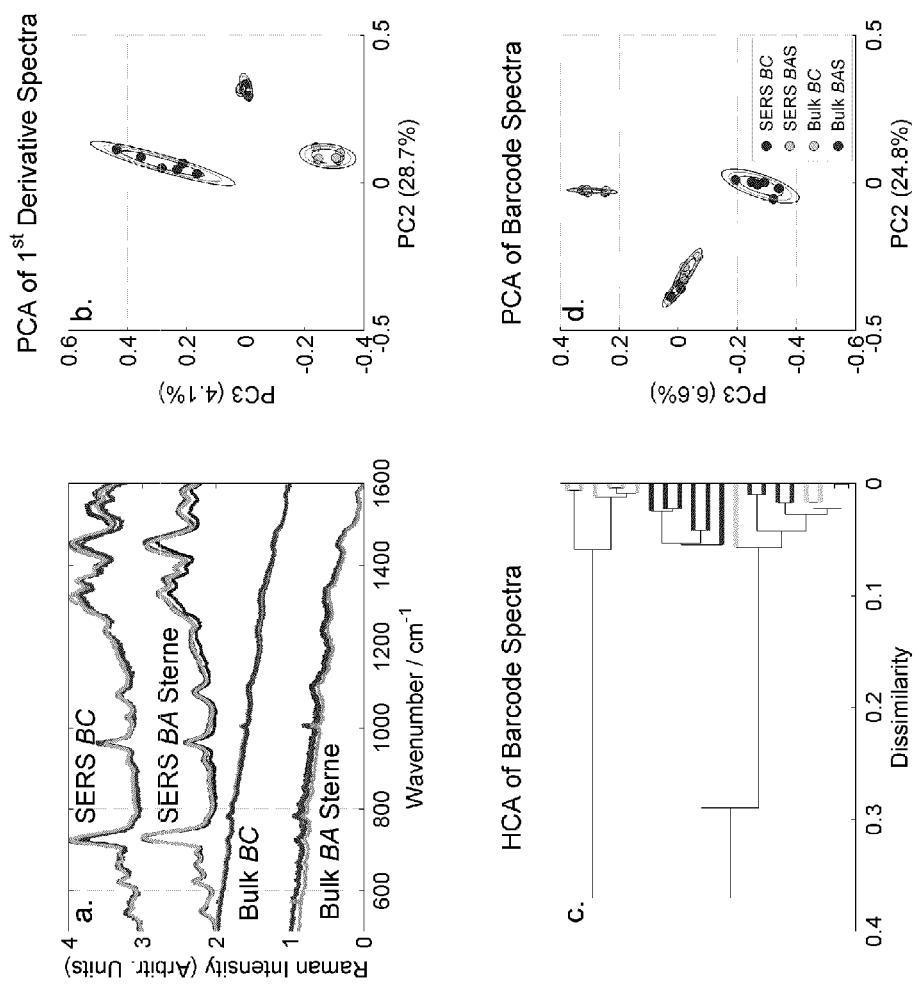
FIG. 11A is a graph illustrating SERS and non-SERS bulk spectra of *B. cereum* (BC) and *B. anthracis* Sterne (BA Sterne).
FIG. 11B is a PCA plot of the corresponding first derivative SERS and non-SERS spectra of *B. cereum* (BC) and *B. anthracis* Sterne (BA Sterne).
FIG. 11C is a HCA dendrogram of SERS and non-SERS PCA clusters resulting from the barcode treatment of the spectra shown in FIG. 11A.
FIG. 11D is a PCA barcode clustering of SERS and bulk BC and BAS spectra corresponding to FIGS. 11A-11C.

The results of a PCA treatment of SERS and bulk Raman signatures are displayed in FIGS. 10 and 11, which dramatically illustrate the enhanced bacterial specificity afforded by SERS vibrational signatures as compared to bulk Raman data. A PC clustering analysis was carried out for bulk (non-SERS) and SERS spectra of *S. typhimurium* and *E. coli* displayed in FIG. 10A. The corresponding first derivative spectra were used as input vectors to the clustering algorithm resulting in the PC2 vs. PC3 plot displayed in FIG. 10B. When the first derivative spectra are used the SERS spectra form separate clusters while the non-SERS spectra significantly overlap. When the PCA of the second derivative barcodes is carried out for these two species, well-separated clusters of *S. typhimurium* and *E. coli* SERS spectra are obtained again but only slightly separated clusters corresponding to the non-SERS (bulk) Raman signatures are evident (FIG. 10D). This same result is represented in the HCA dendrogram (FIG. 10C) resulting from this barcode PCA treatment. The branch point indicating discrimination between the two groups of SERS spectra occurs at a much larger dissimilarity score (~0.35) than that of the corresponding bulk spectra (~0.025). The use of this multivariate data analysis approach highlights how much more distinct the SERS spectral signatures are compared to the normal bulk Raman spectra.

The analogous results are shown in FIG. 11 for SERS and non-SERS spectra of *B. cereus* and *B. anthracis* Sterne. As discussed previously a broad fluorescent background is observed in the 785 nm excited emission of the bulk *bacillus* bacteria (FIG. 11A). The PCA plots clearly show how the SERS spectra of these two closely related species form widely separated clusters and properly identified groupings in the HCA barcode-based dendrogram. In contrast, the non-SERS spectra of *B. cereus* and *B. anthracis* Sterne are not well separated and are incorrectly grouped in the HCA dendrogram resulting from the barcode PCA treatment. An additional contributing factor for the greater difficulty in HCA classification may be the lower signal to noise of the non-SERS spectra as compared to the SERS spectra due to the large fluorescence background exclusively observed in the bulk Raman emission.

These results illustrate an important property of the SERS optical approach for bacterial identification in addition to the attributes of sensitivity, speed, ease of use and portability. Due to the distance dependence of the SERS enhancement mechanisms, only the outer layer of bacterial cells contributes to these SERS spectra. Non-SERS Raman (and IR) vibrational spectra of bacteria have spectral intensities generated by all cellular components; the cytoplasm, where most of the biomass resides, as well as the outer wall layers. Due to the relative number density of these components the cytoplasm contributions will significantly overwhelm the outer layer components in these non-SERS spectra. That the outer layers of bacteria are more chemically distinct than their corresponding cytoplasm components and hence bacterial SERS spectra more species/strain specific than non-SERS, appears consistent with the view that closely related species, such as the *cereus* group of *Bacillus* bacteria, have successfully evolved to occupy different environmental niches while maintaining nearly the same cytoplasmic composition. Thus, they are most distinct where they interact with the outside world and SERS spectral analysis fortuitously, is based on these distinctions, which enhances its diagnostic specificity.

In order to fully exploit the sensitivity and selectivity that SERS offers for bacterial identification rapid, robust spectral analysis protocols employing reference library information must be optimized. Multivariate procedures are required to achieve accurate diagnosis and maximized selectivity based on these vibrational fingerprints. PCA algorithms based on the sign of the second derivative of bacterial SERS spectra observed on the Au nanoparticle covered $SiO_2$ substrates developed in this laboratory are shown to result in clusters that show high selectivity and improved reproducibility as compared to spectral intensity, first or second derivative-based inputs. Both excellent species and strain specificity is obtained with these SERS spectral based barcodes in PCA, HCA or DFA clustering approaches. Furthermore, clustering analysis allows the observed SERS bacterial reproducibility and specificity achievable due to the sol-gel in situ grown gold nanoparticle substrate and the data reduction methodology to be compared with prior SERS studies as judged by the intragroup and intergroup distances respectively. The second derivative-based barcode analysis shown here provides enhanced specificity and reproducibility compared to previously reported SERS bacterial multivariate analyses as judged by these distance criteria.

The success of the second derivative barcodes argues firstly that relative intensities and slowly varying background corrections contribute non-essential variances to the data analysis of these SERS spectra. The consistent trend we observe, as the examples shown here demonstrate, is that clustering improves as the input vectors to the bacterial PCA analysis progress from SERS spectral intensities, to first derivative spectra, second derivative spectra and finally to simply upward (0/1) or downward (1/0) curvature as a function of scattered frequency. The sign of the second derivative of the spectrum is an extremely robust identification feature, subject to minimal variability, for the SERS spectra of bacteria acquired on the sol-gel substrate used here. First derivative spectra avoid contributions resulting from fluctuations in spectral background, but are still apparently sensitive to SERS vibrational intensity fluctuations. Second derivative spectra similarly minimizes background variability and tend to further reduce sensitivity to intensity fluctuations as shown here. Further bacterial SERS spectral reduction to the binary second derivative representation (barcodes) eliminates even further signal fluctuations due all the sources of intensity variations contributing to these spectra.

Developing SERS for rapid and reagentless bacterial identification by use of a reference library of bacterial spectral data is inherently a supervised multivariate analysis technique since it uses a priori knowledge and thus, an inherently supervised approach such as DFA would seem most appropriate for this classification procedure. However, the standard DFA algorithms used to enhance the ratio of between group to intragroup variance may inadvertently enhance false positive rates, as demonstrated here. In other words, the rotation of PCs that results in improved classification of identified groups in DFA treatments does not necessarily result in DF coordinates that maximize the variance for nongroup member PCs. Unsupervised clustering algorithms, which just characterize the variance in a given training set, are less sensitive to such false positive classifications. Thus, the results described herein indicate the potential for false positive bacterial diagnosis due to such simple supervised multivariate protocols.

The PCA analysis of the bacterial SERS and non-SERS vibrational fingerprints of a given species results in clusters which demonstrate the enhanced specificity as well as sensitivity obtained from the SERS approach. The outer layers of bacteria, which contribute the dominant character of SERS signatures owing to the distance dependence of the SERS enhancement mechanisms, are evidently more chemically distinct than the cytoplasm. Characteristics such as drug resistance, some of which depends on the presence of particular surface features, thus can be amenable to SERS identification even for very closely related strains.

The molecular origin of the bacterial SES fingerprints observed is a modern challenge. For example, the generally most intense vibrational band which is seen at about 730 cm$^{-1}$ is one of the most ubiquitous features of bacterial SERS spectra. However, its molecular origin has variously been assigned to adenosine ring stretch, or glucosidic ring in NAG/NAM, components of the cell surface polysaccharide layer. A large (~10 cm$^{-1}$) downshift can be observed when *Bacillus anthracis* is fed nitrogen-15 labeled culture broth consistent with the assignment of a C-N stretching feature to this band. Establishing the molecular origins of these bands arising from cell surface components can be useful for exploiting SERS as a probe of cell surface structures in general and the differences between closely related strains with corresponding different virulence factors in particular.

While the invention has been shown and described with reference to specific embodiments, it should be understood by those skilled in the art that various changes in form and detail may be made therein without departing from the spirit and scope of the invention.

What is claimed is:

1. A computer-implemented method of identifying a material, comprising:
   receiving, by a computer, a spectrum;
   generating from the spectrum a second derivative of the spectrum that highlights a shape of peaks and troughs of the spectrum;
   generating, by a computer, a barcode from a sign of a second derivative of the spectrum;
   performing, by a computer, a multivariate data analysis based on the barcode to identify a grouping of the spectrum; and
   identifying, by a computer, the material from results of the multivariate data analysis including the identification or classification of the grouping of the spectrum based on the barcode.

2. The computer-implemented method of claim 1, wherein the sign of the second derivative is determined from the observed intensity of the spectrum as a function of frequency.

3. The computer-implemented method of claim 1, wherein the barcode includes at least one of a first barcode value assigned for a positive second derivative and a second barcode value assigned for a negative second derivative.

4. The computer-implemented method of claim 1, wherein the spectrum is at least one of a Raman, resonance Raman, neutron scattering, FTIR, and IR spectrum.

5. The computer-implemented method of claim 1, wherein the spectrum is a surface-enhanced Raman spectroscopy (SERS) spectrum.

6. The computer-implemented method of claim 1, wherein the spectrum is received raw input data results derived from at least one of mass spectrometry and chromatography measurements.

7. The computer-implemented method of claim 1, wherein performing the multivariate analysis includes performing a principal component analysis (PCA) clustering process based on the sign of the second derivative of the spectrum.

8. The computer-implemented method of claim 1, wherein the identified material is a chemical or biological agent.

9. The computer-implemented method of claim 1, wherein at least one of a PCA plot and a HCA dendrogram is generated in response to the multivariate analysis process.

10. The computer-implemented method of claim 1, wherein performing the multivariate analysis comprises performing at least one of a supervised clustering technique and an unsupervised clustering technique.

11. A system for identifying a material, comprising:
    a barcode converter that receives a spectrum and generates a barcode based on a sign of a second derivative of the spectrum, wherein the second derivative of the spectrum highlights a shape of peaks and troughs of the spectrum; and
    a spectra analyzer that performs multivariate data analysis on the barcode to identify a grouping of the spectrum, and
    a computer that identifies the material from results of the multivariate data analysis including the identification or classification of the grouping of the spectrum based on the barcode.

12. The system of claim 11, wherein the spectra analyzer includes a clustering processor, which executes clustering technique processes for classifying the spectra into correct clusters.

13. The system of claim 12, wherein the clustering processor performs a multivariate data analysis classification process based on the sign of the second derivative of the spectrum.

14. The system of claim 11, wherein the barcode includes at least one of a first barcode value assigned for a positive second derivative and a second barcode value assigned for a negative second derivative.

15. The system of claim 11, wherein the spectrum is at least one of a Raman, resonance Raman, surface-enhanced Raman spectroscopy (SERS), neutron scattering, FTIR, and IR spectrum.

16. The system of claim 11, wherein performing a multivariate analysis includes performing a principal component analysis (PCA) clustering process based on the sign of the second derivative of the spectrum.

17. The system of claim 11, wherein the identified material is a chemical or biological agent.

18. The system of claim 11, wherein at least one of a PCA plot and a HCA dendrogram is generated in response to the multivariate analysis process.

19. The system of claim 11, wherein performing the multivariate analysis comprises performing at least one of a supervised clustering technique and an unsupervised clustering technique.

* * * * *